United States Patent
Xu et al.

(10) Patent No.: US 12,252,595 B2
(45) Date of Patent: Mar. 18, 2025

(54) PREPARATION METHOD OF 4D CHITOSAN-BASED THERMOSENSITIVE HYDROGEL

(71) Applicant: QINGDAO UNIVERSITY, Shandong (CN)

(72) Inventors: Wenhua Xu, Shandong (CN); Yanhan Dong, Shandong (CN); Lixia Zhang, Shandong (CN); Yuqiao Fan, Shandong (CN)

(73) Assignee: QINGDAO UNIVERSITY, Qingdao (CN)

( * ) Notice: Subject to any disclaimer, the term of this patent is extended or adjusted under 35 U.S.C. 154(b) by 510 days.

(21) Appl. No.: 16/984,626

(22) Filed: Aug. 4, 2020

(65) Prior Publication Data

US 2021/0079170 A1    Mar. 18, 2021

(51) Int. Cl.

| | |
|---|---|
| C08J 3/075 | (2006.01) |
| A61L 27/20 | (2006.01) |
| A61L 27/36 | (2006.01) |
| A61L 27/38 | (2006.01) |
| A61L 27/52 | (2006.01) |
| A61L 27/56 | (2006.01) |
| B33Y 40/20 | (2020.01) |
| B33Y 80/00 | (2015.01) |
| C08J 3/24 | (2006.01) |
| B29C 64/112 | (2017.01) |
| B29K 105/00 | (2006.01) |

(52) U.S. Cl.
CPC ............... *C08J 3/075* (2013.01); *A61L 27/20* (2013.01); *A61L 27/3675* (2013.01); *A61L 27/3687* (2013.01); *A61L 27/3834* (2013.01); *A61L 27/52* (2013.01); *A61L 27/56* (2013.01); *B33Y 40/20* (2020.01); *B33Y 80/00* (2014.12); *C08J 3/24* (2013.01); *A61L 27/3604* (2013.01); *A61L 2430/16* (2013.01); *B29C 64/112* (2017.08); *B29K 2089/00* (2013.01); *B29K 2105/0061* (2013.01); *C08J 2305/08* (2013.01)

(58) Field of Classification Search
None
See application file for complete search history.

(56) References Cited

U.S. PATENT DOCUMENTS

2020/0237963 A1* 7/2020 Miao ..................... A61L 27/50

FOREIGN PATENT DOCUMENTS

| CN | 104958252 A | * 10/2015 | ........... A61K 31/722 |
|---|---|---|---|
| CN | 106177989   | 12/2016 | |
| CN | 106177989 A | 12/2016 | |
| CN | 108409989   | 8/2018  | |
| CN | 108409989 A | 8/2018  | |
| CN | 108484940   | 9/2018  | |
| CN | 108484940 A | 9/2018  | |
| CN | 109749025   | 5/2019  | |
| CN | 109749025 A | 5/2019  | |
| IN | 201721037191 A | * 7/2019 | ........... A61K 31/722 |

OTHER PUBLICATIONS

Zolfagharian, A., Kaynak, A., Khoo, S. Y., & Kouzani, A. (2018). Pattern-driven 4D printing. Sensors and Actuators A: Physical, 274, 231-243. (Year: 2018).*
Galante, R., Rediguieri, C. F., Kikuchi, I. S., Vasquez, P. A., Colaço, R., Serro, A. P., & Pinto, T. J. (2016). About the sterilization of chitosan hydrogel nanoparticles. PLoS One, 11(12), e0168862. (Year: 2016).*

* cited by examiner

*Primary Examiner* — Dale R Miller

(57) ABSTRACT

Medical material production and preparation, and a preparation method of a 4D chitosan-based thermosensitive hydrogel. First, chitosan is dissolved in acetic acid solution; a chitosan-based thermosensitive hydrogel is printed by a 4D bioprinter and lyophilized after solvent extraction, to obtain lyophilized chitosan; subsequently, aqueous β-sodium glycerophosphate solution is prepared with ultrapure water and β-sodium glycerophosphate, and then aqueous carboxymethyl chitosan solution is prepared with ultrapure water and aqueous β-sodium glycerophosphate solution are charged into and mixed well with aqueous carboxymethyl chitosan solution to prepare a mixture; finally, the lyophilized chitosan is crosslinked with the mixture to obtain the 4D chitosan-based thermosensitive hydrogel. With scientific and reliable principles thereof, the present invention solves a problem that conventional thermosensitive hydrogels have uneven pore sizes, and improves the entrapment efficiency and ability of limbal stem cells.

3 Claims, 2 Drawing Sheets

PREPARATION METHOD OF 4D CHITOSAN-BASED THERMOSENSITIVE HYDROGEL

CROSS REFERENCE TO RELATED APPLICATIONS

This application claims priority to Chinese Patent Application No. 201910871003.5 filed Sep. 16, 2019. The contents of this prior application are incorporated herein by reference.

TECHNICAL FIELD

The present invention belongs to the technical field of medical material production and preparation, and relates to a preparation method of a 4D chitosan-based thermosensitive hydrogel. The method is to prepare a chitosan-based thermosensitive hydrogel for alkali burn repair based on 4D printing technology.

BACKGROUND

There are a variety of corneal injuries. Particularly, it is difficult to treat chemical damage clinically. Corneal alkali burn is a relatively severe chemical injury, causing corneal epithelial necrosis and defects, corneal and conjunctival melting and perforation, symblepharon, etc.; also, accompanied by formation of plentiful new capillaries, severe patients may suffer from corneal blindness. So far, the disease is principally treated with keratoplasty or amniotic membrane transplantation clinically. However, the former is facing two major problems: lack of donor and immunological rejection. For the latter, cornea, as a basement membrane, can develop autolysis easily due to degradation by collagenases accumulated in wounded tissues after severe corneal injury, such as alkali burn, so that patients achieve poor outcomes even if they have undergone multiple transplantations. Therefore, how to repair corneal epithelial defects and reduce corneal neovascularization and scar formation is an urgent issue to be solved.

Biogel-supported limbal stem cells prepared by tissue engineering methods have some effects on corneal wound healing, but irregular network structure and uneven pore size exhibited on the gel surface under SEM directly influence the entrapment efficiency of limbal stem cells. For example, a preparation method of a tilmicosin inclusion compound chitosan temperature-sensitive gel disclosed by Chinese Patent Application No. 201610837528.3 includes the following steps: (1) weighing chitosan, dissolving the chitosan in 0.1 mol/L hydrochloric acid and sufficiently stirring the hydrochloric acid until completely dissolving the chitosan, to obtain a 10 mg/mL to 20 mg/mL chitosan solution; dissolving sodium glycerophosphate in deionized water, to obtain a 0.2 g/mL to 1.0 g/mL sodium glycerophosphate solution; dripping the sodium glycerophosphate solution into the chitosan solution to mix; adjusting the pH (potential of hydrogen) value of mixed solution to 7.1 to 7.4; uniformly stirring the obtained mixed solution at the temperature of 4° C. to obtain chitosan temperature-sensitive gel; (2) weighing HP-β-CD in a mortar, weighing water in a mass ratio of water to HP-β-CD of (2-5):1 to dissolve HP-β-CD; weighing tilmicosin in a mortar in a mass ratio of HP-β-CD to tilmicosin of 2:1, mixing and grinding at 20° C. for 30 min to obtain white powders, and sieving through an 80-mesh sieve to obtain a tilmicosin inclusion compound; (3) adding the chitosan temperature-sensitive gel obtained in step (1) into a conical flask, weighing the tilmicosin inclusion compound obtained in step (2) in the conical flask, and uniformly stirring the tilmicosin inclusion compound and the chitosan temperature-sensitive gel in a magnetic stirrer at normal temperature to obtain the tilmicosin inclusion compound chitosan temperature-sensitive gel. The mass fraction of tilmicosin in the tilmicosin inclusion compound chitosan temperature-sensitive gel is 9.9% to 10%. The tilmicosin inclusion compound chitosan temperature-sensitive gel is stored at 4° C.

On Feb. 25, 2013, at TED2013 held in California, the USA, Skylar Tibbits from Massachusetts Institute of Technology showed attendees a 4D printing technology through a complete experiment and elaborated the technology by means of the experiment. In view of the so-called 4D printing, more precisely, a self-deforming material can be automatically folded into the corresponding shape according to a product design merely under certain conditions (such as temperature, humidity, etc.), without connecting to any complex electromechanical equipment. 4D printing is a technology that uses a 3D printer to print deformable materials. The 4D printing technology has been introduced into the technical field of gel preparation. A 4D printing method of programmable deformation tough hydrogel disclosed by Chinese Patent Application No. 201810208715.4 includes the following steps: (1) adding a mixed solution of acrylamide and acrylic acid to a temperature initiator and a pro-initiator, and holding in an incubator, to obtain a poly-(acrylic-co-acryl amide) copolymer solution; adding a mixed solution of acrylic acid and N-isopropylacrylamide to a temperature initiator and a pro-initiator, and holding in the incubator, to obtain a poly-(acryl amide-co-N-isopropylacrylamide) copolymer solution; (3) mixing the poly-(acrylic-co-acryl amide) copolymer solution with the poly-(acryl amide-co-N-isopropylacrylamide) copolymer solution to obtain mixed solutions of poly-(acrylic-co-acryl amide) and poly-(acryl amide-co-N-isopropylacrylamide) copolymers at two ratios, where one solution with high-level poly-(acryl amide-co-N-isopropylacrylamide) copolymer component is used as a salt-sensitive material to drive deformation, and the other is used as a binder of poly-(acrylic-co-acryl amide) copolymer solution to salt-sensitive mixed solution; (4) using a 3D printing platform, extruding the poly-(acrylic-co-acryl amide) copolymer and the mixed solution of poly-(acrylic-co-acryl amide) and poly-(acryl amide-co-N-isopropylacrylamide) copolymers onto a glass substrate to acquire a corresponding space shape structure according to preset print parameters, respectively; (5) placing the printed shape structure into a Fe(III) ion solution of the incubator to crosslink, and subsequently placing the gel soaked in the Fe(III) ion solution into a deionized aqueous solution of the incubator to further crosslink to obtain an equilibrium gel structure; and (6) deforming the equilibrium gel structure in concentrated saltwater to obtain a predesigned shape structure. A method for preparing a temperature driven programmable 4D printing intelligent material disclosed by Chinese Patent Application No. 201810280579.X includes the following steps: (I) Preparation of high-density 4D intelligent thermosensitive hydrogel material: a) composition of raw materials of the high-density 4D intelligent thermosensitive hydrogel material: using N-isopropylacrylamide as a monomer, XLG synthetic magnesium lithium silicate as a crosslinking agent, potassium persulfate as an initiator, N,N,N',N'-tetraethylethylenediamine as a catalyst, and wood nanocellulose as a reinforced phase, where a molar ratio of monomer: initiator: catalyst is 100:0.370:0.638, a concentration of the wood nanocellulose is 3 to 5 mg/mL, and a mass fraction of the crosslinking agent is 3 wt. % to 3.5 wt. %; b) blending: weighing raw materials in the mixture ratio as described in step a), stirring the wood nanocellulose in an ice/water bath for 30 to 40 min, and subsequently sonicating for 10 to 15 min; subsequently, adding XLG synthetic magnesium lithium silicate, and stirring for 60 to 65 min; subsequently, adding N-isopropylacrylamide, and stirring for 120 to 130 min; finally, adding potassium persulfate and N,N,N',N'-tetraethylethylenediamine successively, and stirring for 5 to 6 min; c) injecting the well-mixed material in step b) into an assembled die, striking off, sealing the die, and allowing the die to stand at 25 to 27° C. for 24 to 26 h for molding. (II) Synthesis of temperature driven programmable 4D printing intelligent material: a) composition of raw materials of the low-density 4D intelligent thermosensitive hydrogel: using N-isopropylacrylamide as a monomer, XLG synthetic magnesium lithium silicate as a crosslinking agent, potassium persulfate as an initiator, N,N,N',N'-tetraethylethylenediamine as a catalyst, and wood nanocellulose as a reinforced phase, where a molar ratio of monomer: initiator: catalyst is 100: 0.370:0.638, a concentration of the wood nanocellulose is 0 to 2 mg/mL, and a mass fraction of the crosslinking agent is 3 wt. % to 3.5 wt. %; b) blending: weighing raw materials in the mixture ratio as described in step (a), stirring the wood nanocellulose in an ice/water bath for 30 to 40 min, and subsequently sonicating for 10 to 15 min; subsequently, adding XLG synthetic magnesium lithium silicate, and stirring for 60 to 65min; subsequently, adding N-isopropylacrylamide, and stirring for 120 to 130 min; finally, adding potassium persulfate and N,N,N',N'-tetraethylethylenediamine successively, and stirring for 5 to 6 min; c) injecting the well-mixed low-density 4D intelligent thermosensitive hydrogel in step b) into an assembled die, placing above the high-density 4D intelligent thermosensitive hydrogel, striking off, sealing the die, and allowing the die to stand at 25 to 27° C. for 24 to 26 h for molding. Heretofore, the temperature driven programmable 4D printing intelligent material is prepared successfully. A preparation method of a 4D printing self-combined hydrogel material disclosed by Chinese Patent Application No. 201910141257.1 includes the following steps: I, synthesizing CD-acrylamide: dissolving cyclodextrins (CDs) with side groups substituted by amino groups in a weak basic solution, adjusting the solution to pH 8 to pH 10 with a basic inorganic matter, adding anhydrides, stirring at 40 to 80° C. for 4 to 8 h, evaporating 90% to 95% of water from the solution, subsequently washing with organic solvent I, centrifuging, collecting precipitates, and vacuum drying to obtain CD-acrylamide, where the cyclodextrins with side groups substituted by amino groups in step I may be 6-amino-a-CD, 3-amino-a-CD, or 6-amino-β-CD; II, synthesizing azo-acrylamide: dissolving azobenzenes and amines in organic solvent II, subsequently heating to 20 to 50° C., and adding anhydrides, to obtain a mixed solution; subsequently, stirring the mixed solution at 60 to 65° C. for 3 to 5 h, filtering, removing precipitates, concentrating filtrates under vacuum, and recrystallizing with organic solvent III, to obtain azo-acrylamide, where azobenzenes may be p-aminoazobenzene or azobenzene-based polyacrylamide, and amines may be triethanolamine or trimethylamine; III, polymerizing free radicals into a gel: putting a free radical polymerized monomer, the CD-acrylamide obtain in step I, the azo-acrylamide obtained in step II and a monomer for intensifying chain rigidity into organic solvent IV, stirring well, heating to 60 to 80° C., adding an initiator, reacting under stirring at 60 to 80° C. for 15 to 20 h, stopping stirring, and subsequently holding at 60 to 65° C. for 1 to 5 h, to obtain the 4D printing self-combined hydrogel material, where the free radical polymerized monomer may be acrylic acid, acrylamide, or methacrylate, and the monomer for intensifying chain rigidity may be N-vinyl carbazole or styrene. Therefore, developing a preparation method of a 4D chitosan-based thermosensitive hydrogel to improve the entrapment efficiency of limbal stem cells is of high social significance and practical value.

SUMMARY

An objective of the present invention is to overcome the defects in the prior art and develop a preparation method of a 4D chitosan-based thermosensitive hydrogel, so as to prepare a 4D chitosan-based thermosensitive hydrogel improving the entrapment efficiency of limbal stem cells effectively and promoting alkali-burned corneal epithelial reconstruction.

To achieve the above objective, the preparation method of a 4D chitosan-based thermosensitive hydrogel as provided by the present invention includes the following steps:

at room temperature, weighing chitosan, dissolving the chitosan in acetic acid solution, stirring until the chitosan has completely dissolved, to obtain a chitosan solution; using a 4D bioprinter to print the chitosan solution into a chitosan-based thermosensitive hydrogel with a pore size of 50 to 100 μm according to preset print parameters, and shaping the chitosan-based thermosensitive hydrogel as desired; lyophilizing after solvent extraction, to obtain lyophilized chitosan;

charging ultrapure water and β-sodium glycerophosphate into a water bath kettle at 60 to 70° C.; after dissolution of β-sodium glycerophosphate, naturally cooling to room temperature to obtain an aqueous β-sodium glycerophosphate solution;

preparing an aqueous carboxymethyl chitosan solution with ultrapure water at room temperature, dripping the aqueous β-sodium glycerophosphate solution obtained in step (2) dropwise into the aqueous carboxymethyl chitosan solution, and mixing well to obtain a mixture; and crosslinking the lyophilized chitosan obtained in step (1) with the mixture obtained in step (3) for 1 to 2 min, to obtain the 4D chitosan-based thermosensitive hydrogel of uniform pore size.

In the present invention, a molar concentration of the acetic acid solution described in step (1) is 0.2 Mol/L, and a concentration of the chitosan solution ranges from 2.2 wt. % to 6.7 wt. %; a concentration of the aqueous β-sodium glycerophosphate solution ranges from 6 wt. % to 8 wt. %; a concentration of the aqueous carboxymethyl chitosan solution prepared in step (3) ranges from 2.2 wt. % to 6.7 wt. %; concentrations of the chitosan, the carboxymethyl chitosan, and the β-sodium glycerophosphate in the 4D chitosan-based thermosensitive hydrogel prepared in step (4) are 10 wt. % to 30 wt. %, 10 wt. % to 30 wt. %, and 60 wt. % to 80 wt. %, respectively.

In the present invention, the 4D chitosan-based thermosensitive hydrogel may be preserved in a sterile environment at 4 to 15° C. for 6 to 12 months.

After entrapping limbal stem cells, the 4D chitosan-based thermosensitive hydrogel prepared in the present invention is applied on the surface of an alkali burned cornea and releases limbal stem cells to repair and treat a wound.

Compared with the prior art, the present invention applies the 4D bioprinting technology to the preparation of the chitosan-based thermosensitive hydrogel; using the chitosan-based thermosensitive hydrogel of uniform pore size as a transplantation scaffold of limbal stem cells can effectively improve the entrapment efficiency of limbal stem cells, and promote alkali-burned corneal epithelial reconstruction. With scientific and reliable principles thereof, the present invention solves a problem that conventional thermosensitive hydrogels have uneven pore sizes, and improves the entrapment efficiency and ability of limbal stem cells; the present invention has important theoretical significance and broad application prospects in the field of corneal wound healing, providing help for patients who require repair of corneal alkali burns in clinical medicine.

DETAILED DESCRIPTION

The present invention is described in detail below with reference to the accompanying drawings and specific examples.

Example 1

Figure 1:
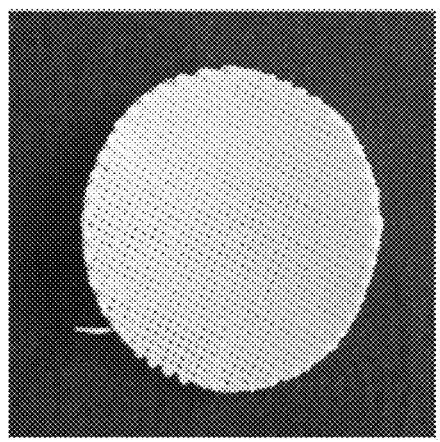
FIG. 1 illustrates the structure of chitosan described in step (1) of Example 1 of the present invention.
Figure 2:
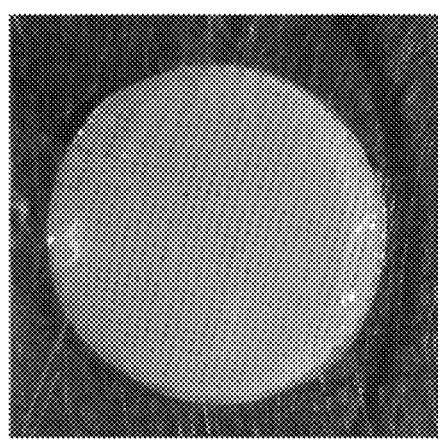
FIG. 2 illustrates the structure of a 4D chitosan-based thermosensitive hydrogel described in step (4) of Example 1 of the present invention.
Figure 3:
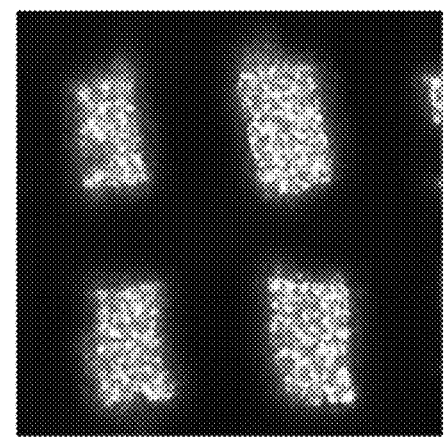
FIG. 3 illustrates the state of a 4D chitosan-based thermosensitive hydrogel entrapping limbal stem cells at 40-fold magnification described in Example 2 of the present invention.
Figure 4:
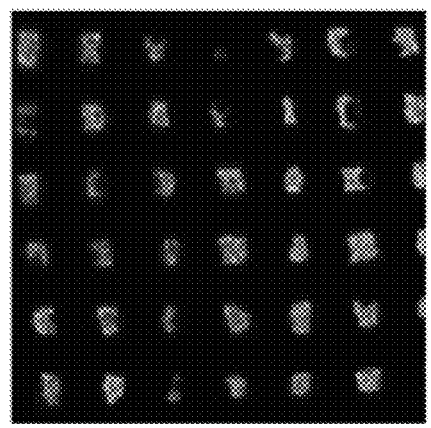
FIG. 4 illustrates the state of the 4D chitosan-based thermosensitive hydrogel entrapping limbal stem cells at 10-fold magnification described in Example 2 of the present invention.

A preparation method of a 4D chitosan-based thermosensitive hydrogel as provided by the example included the following steps:

at room temperature, weighing chitosan, dissolving the chitosan in 0.2 Mol/L acetic acid solution, stirring for 12 h until the chitosan had completely dissolved, to obtain a 4.4 wt. % chitosan solution; printing the chitosan solution into round chitosan-based thermosensitive hydrogel with a pore size of 50 to 100 μm according to preset print parameters (hole interval 600 μm, layer height 100 μm, bed temperature −25° C., printing speed 15 mm/s, nozzle diameter 0.3 mm, and output 0.1 g/min) by means of a UN-4DBI-C01 4D bioprinter; lyophilizing after solvent extraction, to obtain lyophilized chitosan, as shown in FIG. 1;

charging ultrapure water and β-sodium glycerophosphate into a water bath kettle at 65° C.; after dissolution of β-sodium glycerophosphate, naturally cooling to room temperature to obtain a 7 wt. % aqueous β-sodium glycerophosphate solution;

preparing a 4.4 wt. % aqueous carboxymethyl chitosan solution with ultrapure water at room temperature; dripping the aqueous β-sodium glycerophosphate solution obtained in step (2) dropwise into the aqueous carboxymethyl chitosan solution, and mixing well to obtain a mixture; and crosslinking the lyophilized chitosan obtained in step (1) with the mixture obtained in step (3) for 1 to 2 min, to obtain a 4D chitosan-based thermosensitive hydrogel of uniform pore size as shown in FIG. 2, where concentrations of the chitosan, the carboxymethyl chitosan, and the β-sodium glycerophosphate in the 4D chitosan-based thermosensitive hydrogel were 18 wt. %, 18 wt. %, and 64 wt. %, respectively.

Example 2

This example relates to a process of the 4D chitosan-based thermosensitive hydrogel prepared in Example 1 entrapping limbal stem cells:

The 4D chitosan-based thermosensitive hydrogel was placed and fully soaked in a Petri dish to obtain a 4D chitosan-based thermosensitive hydrogel to be entrapped.

Limbal stem cells were separated, cultured, and charged into the 4D chitosan-based thermosensitive hydrogel to be entrapped as obtained in step (1) for further culture.

After 24 h culture, the state of the 4D chitosan-based thermosensitive hydrogel entrapped limbal stem cells were observed under a microscope at 40- and 10-fold magnification, respectively.

Example 3

This example relates to a comparative test of efficacy of 4D chitosan-based thermosensitive hydrogel-entrapped limbal stem cells versus conventional thermosensitive hydrogel-entrapped limbal stem cells in the treatment of rabbits with corneal alkali burns.

Corneas of living rabbits were subject to alkali burns to obtain animal models of alkali burns.

The animal models of alkali burns obtained in step (1) were treated with conventional thermosensitive hydrogel-entrapped limbal stem cells, to obtain models of treatment with conventional thermosensitive hydrogel.

The animal models of alkali burns obtained in step (1) were treated with 4D chitosan-based thermosensitive hydrogel-entrapped limbal stem cells prepared in Example 1, to obtain models of treatment with 4D chitosan-based thermosensitive hydrogel.

Figure 5:
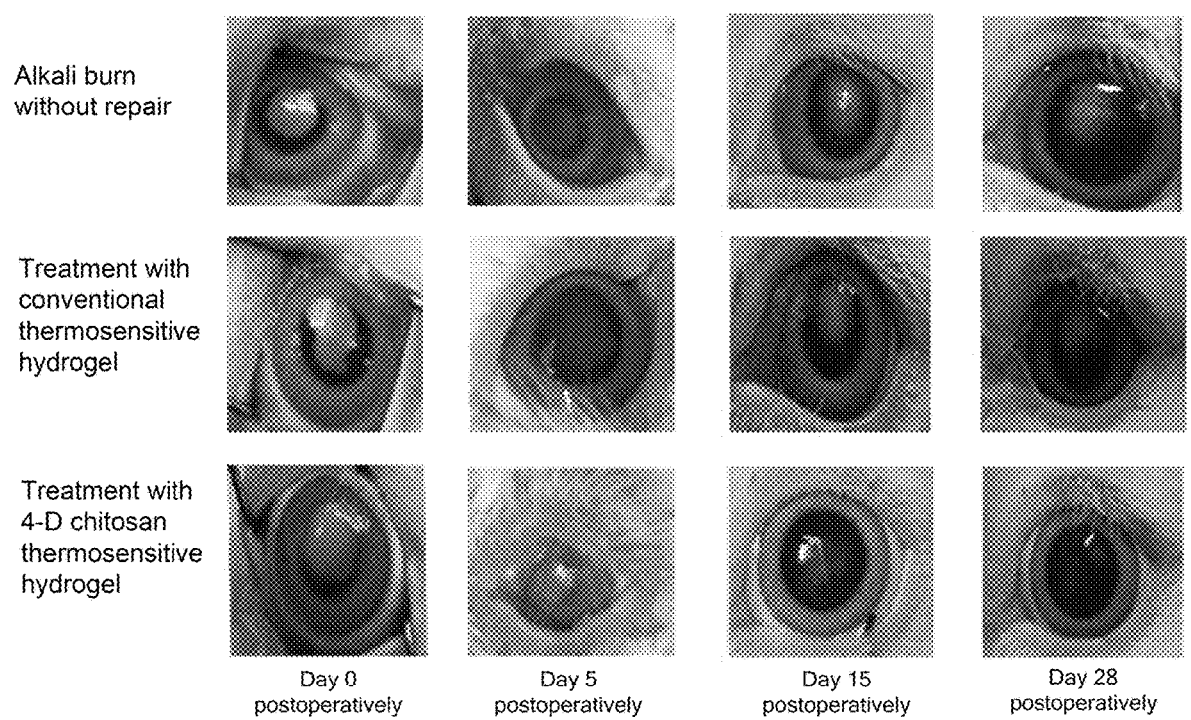
FIG. 5 illustrates the comparison of efficacy of conventional thermosensitive hydrogel-entrapped limbal stem cells versus 4D chitosan-based thermosensitive hydrogel-entrapped limbal stem cells in the treatment of rabbits with corneal alkali burns.

Efficacy of both models was observed 28 days after treatment, respectively. As shown in FIG. 5, after alkali burns procedure, corneal wound areas (white areas in the figure) of each group decrease gradually over time; moreover, 4D chitosan-based thermosensitive hydrogel treatment group has significantly better repairing effect than both conventional thermosensitive hydrogel group and non-repairing group.

What is claimed:

1. A preparation method of a chitosan-based hydrogel, comprising the following steps:
(1) at room temperature, weighing chitosan, dissolving the chitosan in acetic acid solution, stirring until the chitosan has completely dissolved, to obtain a chitosan solution; using a bioprinter to print the chitosan solution into a chitosan-based hydrogel with a uniform pore size ranging from 50 to 100 μm according to preset print parameters, and shaping the chitosan-based hydrogel as desired; lyophilizing after solvent extraction, to obtain lyophilized chitosan;
wherein a molar concentration of the acetic acid solution in step (1) is 0.2 Mol/L, and a concentration of the chitosan solution is 4.4 wt. %; and (2) changing ultrapure water and β-sodium glycerophosphate into a water bath kettle at 60 to 70° C.; after dissolution of β-sodium glycerophosphate, naturally cooling to room temperature to obtain an aqueous β-sodium glycerophosphate solution;

(3) preparing an aqueous carboxymethyl chitosan solution with ultrapure water at room temperature, dripping the aqueous β-sodium glycerophosphate solution obtained in step (2) dropwise into the aqueous carboxymethyl chitosan solution, and mixing well to obtain a mixture; and (4) crosslinking the lyophilized chitosan obtained in step (1) with the mixture obtained in step (3) for 1 to 2 min, to obtain the chitosan-based hydrogel of uniform pore size;

wherein a concentration of the aqueous β-sodium glycerophosphate solution is 7 wt. %;

wherein a concentration of the aqueous carboxymethyl chitosan solution prepared in step (3) is 4.4 wt %;

wherein a concentration of the carboxymethyl chitosan in the chitosan-based hydrogel prepared in the step (4) is 10 wt. % to 30 wt. %; a concentration of the β-sodium glycerophosphate in the chitosan-based hydrogel prepared in the step (4) is 60 wt. % to 80 wt. %.

2. A preparation method of a chitosan-based hydrogel, comprising the following steps:

(1) at room temperature, weighing chitosan, dissolving the chitosan in acetic acid solution, stirring until the chitosan has completely dissolved, to obtain a chitosan solution; using a bioprinter to print the chitosan solution into a chitosan-based hydrogel with a uniform pore size of 50 μm according to preset print parameters, and shaping the chitosan-based hydrogel as desired; lyophilizing after solvent extraction, to obtain lyophilized chitosan;

wherein a molar concentration of the acetic acid solution in step (1) is 0.2 Mol/L, and a concentration of the chitosan solution is 4.4 wt. %; and (2) changing ultrapure water and β-sodium glycerophosphate into a water bath kettle at 60 to 70° C.; after dissolution of β-sodium glycerophosphate, naturally cooling to room temperature to obtain an aqueous β-sodium glycerophosphate solution;

(3) preparing an aqueous carboxymethyl chitosan solution with ultrapure water at room temperature, dripping the aqueous β-sodium glycerophosphate solution obtained in step (2) dropwise into the aqueous carboxymethyl chitosan solution, and mixing well to obtain a mixture; and (4) crosslinking the lyophilized chitosan obtained in step (1) with the mixture obtained in step (3) for 1 to 2 min, to obtain the chitosan-based hydrogel of uniform pore size;

wherein a concentration of the aqueous β-sodium glycerophosphate solution is 7 wt. %;

wherein a concentration of the aqueous carboxymethyl chitosan solution prepared in step (3) is 4.4 wt %;

wherein a concentration of the carboxymethyl chitosan in the chitosan-based hydrogel prepared in the step (4) is 10 wt. % to 30 wt. %; a concentration of the β-sodium glycerophosphate in the chitosan-based hydrogel prepared in the step (4) is 60 wt. % to 80 wt. %.

3. A preparation method of a chitosan-based hydrogel, comprising the following steps:

(1) at room temperature, weighing chitosan, dissolving the chitosan in acetic acid solution, stirring until the chitosan has completely dissolved, to obtain a chitosan solution; using a bioprinter to print the chitosan solution into a chitosan-based hydrogel with a uniform pore size of 100 μm according to preset print parameters, and shaping the chitosan-based hydrogel as desired; lyophilizing after solvent extraction, to obtain lyophilized chitosan;

wherein a molar concentration of the acetic acid solution in step (1) is 0.2 Mol/L, and a concentration of the chitosan solution is 4.4 wt. %; and (2) changing ultrapure water and β-sodium glycerophosphate into a water bath kettle at 60 to 70° C.; after dissolution of β-sodium glycerophosphate, naturally cooling to room temperature to obtain an aqueous β-sodium glycerophosphate solution;

(3) preparing an aqueous carboxymethyl chitosan solution with ultrapure water at room temperature, dripping the aqueous β-sodium glycerophosphate solution obtained in step (2) dropwise into the aqueous carboxymethyl chitosan solution, and mixing well to obtain a mixture; and (4) crosslinking the lyophilized chitosan obtained in step (1) with the mixture obtained in step (3) for 1 to 2 min, to obtain the chitosan-based hydrogel of uniform pore size;

wherein a concentration of the aqueous β-sodium glycerophosphate solution is 7 wt. %;

wherein a concentration of the aqueous carboxymethyl chitosan solution prepared in step (3) is 4.4 wt %;

wherein a concentration of the carboxymethyl chitosan in the chitosan-based hydrogel prepared in the step (4) is 10 wt. % to 30 wt. %; a concentration of the β-sodium glycerophosphate in the chitosan-based hydrogel prepared in the step (4) is 60 wt. % to 80 wt. %.

* * * * *